USO11952324B2

United States Patent
Khramov et al.

(10) Patent No.: US 11,952,324 B2
(45) Date of Patent: Apr. 9, 2024

(54) AMIDOAMINE SYNTHESIS, METHODS TO TRACK THE REACTION PROCESS

(71) Applicant: M-I L.L.C., Houston, TX (US)

(72) Inventors: Dimitri M. Khramov, Katy, TX (US); Yiyan Chen, Sugar Land, TX (US); Albert Okhrimenko, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1075 days.

(21) Appl. No.: 16/636,017

(22) PCT Filed: Aug. 2, 2018

(86) PCT No.: PCT/US2018/044903
§ 371 (c)(1),
(2) Date: Feb. 2, 2020

(87) PCT Pub. No.: WO2019/028198
PCT Pub. Date: Feb. 7, 2019

(65) Prior Publication Data
US 2021/0323909 A1 Oct. 21, 2021

Related U.S. Application Data

(60) Provisional application No. 62/541,464, filed on Aug. 4, 2017.

(51) Int. Cl.
*C09K 8/035* (2006.01)
*C07C 231/02* (2006.01)
(Continued)

(52) U.S. Cl.
CPC ............ *C07C 231/02* (2013.01); *C09K 8/035* (2013.01); *C09K 8/36* (2013.01); *G01N 30/72* (2013.01); *G01N 2030/025* (2013.01)

(58) Field of Classification Search
CPC ........ C07C 231/02; C09K 8/035; C09K 8/36; G01N 30/72; G01N 2030/025
See application file for complete search history.

(56) References Cited

U.S. PATENT DOCUMENTS

| | | | |
|---|---|---|---|
| 2004/0050790 A1 | 3/2004 | Baarman et al. | |
| 2007/0093393 A1* | 4/2007 | Navarrete | C09K 23/16 507/131 |
| 2015/0080286 A1 | 3/2015 | Kohle et al. | |

FOREIGN PATENT DOCUMENTS

| | | |
|---|---|---|
| WO | 2004/050790 A1 | 6/2004 |
| WO | 2015/012818 A1 | 1/2015 |

OTHER PUBLICATIONS

Preliminary Office Action issued in Brazil Patent Application BR112020002384-1 dated May 3, 2022, 6 pages.
(Continued)

*Primary Examiner* — Deborah D Carr

(57) ABSTRACT

Methods may include quantifying the concentration of residual free amine and/or free carboxylic acid in a product mixture prepared from a reaction of a multireactive species and a fatty reagent; verifying that the concentration for the free amine and/or free acid in the product mixture is within an acceptable threshold for a given application; and combining the product mixture with one or more wellbore fluid components to generate the wellbore fluid. In another aspect, methods may include including reacting the multireactive species and a fatty reactant to generate a product mixture; quantifying the concentration of residual free amine and/or free carboxylic acid in the product mixture; verifying that the concentration for the free amine and/or free acid in the product mixture is within an acceptable threshold for a given application; and collecting the product mixture.

28 Claims, 8 Drawing Sheets

(51) Int. Cl.
*C09K 8/36* (2006.01)
*G01N 30/72* (2006.01)
*G01N 30/02* (2006.01)

(56) References Cited

OTHER PUBLICATIONS

Cummins, et al., "An analytical method for determining bound and free alkanolamines in heat stable salt contaminated solutions," AIChE 1990 Summer National Meeting.

Khimicheskaj entsiklopediaj, pod red. N.S. Zefirova, Nauchnoe izdarelstvo "Bolshaaj Rossiiskay Ensiklopediaj," M. 1995, V. 4, pp. 1187-1190 (without English translation).

Sigma-Aldrich Co., "BSTFA—Product Specification" retrieved on Jan. 28, 2020 at http://www.sigmaaldrich.com/Graphics/Supelco/objects/4800/4746.pdf.

International Search Report and Written Opinion for the counterpart International patent application PCT/US2018/044903 dated Oct. 25, 2018.

Mudiyanselage, Y. et al., "A Dissertation entitled Progress Towards the Production of Bio-sourced Specialty Chemicals", 2016, 178 pages.

Plotka-Wasylka, J. M. et al., "Chemical Derivatization Processes Applied to Amine Determination in Samples of Different Matrix Composition", Chemical Reviews, 2015, 115(11) pp. 4693-4718.

Halket, J. M. et al., "Derivatization in Mass Spectrometry-1. Silylation", European Journal of Mass Spectrometry, 2003, 9(1), pp. 1-21.

International Preliminary Report on Patentability for the counterpart International patent application PCT/US2018/044903 dated Feb. 13, 2020.

* cited by examiner

AMIDOAMINE SYNTHESIS, METHODS TO TRACK THE REACTION PROCESS

This application claims priority to, and the benefit of, U.S. Provisional Patent Application No. 62/541,464, filed Aug. 4, 2017, which is expressly incorporated herein by this reference in its entirety.

BACKGROUND

During wellbore operations, various fluids may be used in the well for a variety of functions. The fluids may be circulated through a bore hole, which may subsequently flow upward through the wellbore to the surface. During this circulation, the drilling fluid may remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

For some wellbore fluids such as oil-based muds, surfactant performance is important for maintaining proper fluid properties under downhole conditions. Optimum performance of wellbore fluids is aided by adequate characterization of each of the constituent chemicals, and for some compounds key intermediates used to benchmark reaction completion and formation of the desired product may have unique characteristics that make quantifying these intermediates difficult using standard analytical techniques. Poor characterization of wellbore fluid components can result in batch-by-batch variation in commercial stocks and can result in poor performance in the field and downstream applications.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to methods that include: quantifying the concentration of residual free amine and/or free carboxylic acid in a product mixture prepared from a reaction of a multireactive species and a fatty reactant, wherein the reaction of a multireactive species and a fatty reactant include an amide- or imine-forming reaction; verifying that the concentration for the free amine and/or free acid in the product mixture is within an acceptable threshold for a given application; and combining the product mixture with one or more wellbore fluid components to generate the wellbore fluid.

In another aspect, embodiments disclosed herein relate to relate to methods that include: quantifying, by nonaqueous titration, the concentration of residual free amine in a product mixture prepared from a reaction of a multireactive species and a fatty reactant, wherein the reaction of a multireactive species and a fatty reactant comprises an amide- or imine-forming reaction; verifying that the concentration for the residual free amine in the product mixture is within an acceptable threshold for a given application; and combining the product mixture with one or more wellbore fluid components to generate the wellbore fluid.

In another aspect, embodiments disclosed herein relate to relate to methods that include: reacting the multireactive species and a fatty reactant to generate a product mixture, wherein reacting the multireactive species and a fatty reactant comprises an amide- or imine-forming reaction; quantifying the concentration of residual free amine and/or free carboxylic acid in the product mixture; verifying that the concentration for the free amine and/or free acid in the product mixture is within an acceptable threshold for a given application; and collecting the product mixture.

Other aspects and advantages of the claimed subject matter will be apparent from the following description and the appended claims.

DETAILED DESCRIPTION

Figure 1:
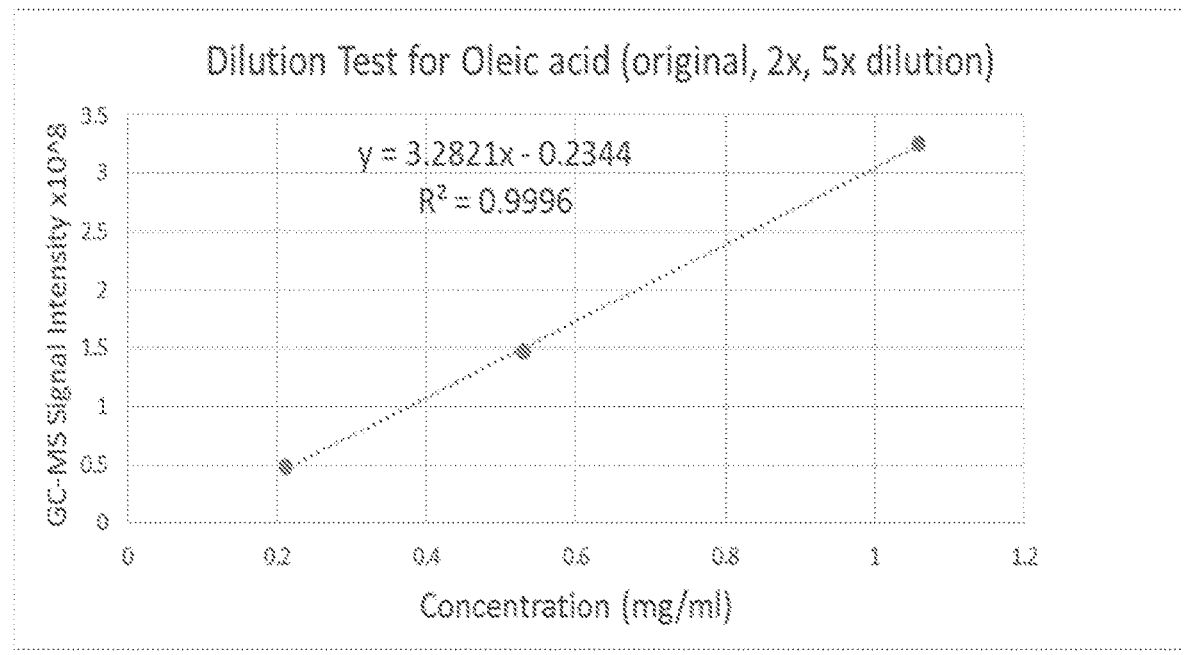
FIGS. 1 and 2 are graphical representations showing signal intensity from a gas-chromatography mass spectrometer as a function of concentration for a sample of fatty reactant in accordance with embodiments of the present disclosure.

In one aspect, embodiments disclosed herein relate to methods of characterizing the products obtained from reactions involving multireactive species that may undergo full or partial conversion during synthesis. In some embodiments, methods may also include determining, which functional sites of the multireactive species have been reacted. In one or more embodiments, methods may include the preparation of drilling or other wellbore fluids and other compositions that include verifying the composition of product mixtures that may contain levels of unreacted components that vary between batches in industrial scale synthesis. In some embodiments, methods in accordance with the present disclosure may be used to identify batch-specific differences in emulsifiers, rheology modifiers, and other additives used in wellbore fluid formulation, with the goal of enhancing formulation performance predictability and reproducibility.

In one or more embodiments, methods of the present disclosure are directed to the analysis of functional additives for wellbore fluids such as emulsifiers produced from multireactive species. The completeness of a reaction used to produce an emulsifier may have a substantial impact on performance of the final fluid composition, particularly in high pressure/high temperature applications. For example, during the synthesis of amidoamine and multiamide emulsifiers, reactant properties such as free amine concentration are used to measure the rate of conversion of the reactants to the final products. However, reaction intermediates and byproducts may form salts and other nonvolatile species that are difficult to detect using conventional quality control measurements. This can result in final products having different levels of fully converted product despite the products having the same nominal free amine number, which manifests as inconsistent performance of amidoamine and multiamide products between batches, and possible across manufacturers. In one or more embodiments, methods in accordance with the present disclosure may be used to verify the product measurements and quantify conversion rates for multireactive species including amidoamines and multiamides, which may allow for consistent performance of products incorporating these chemicals in laboratory and field settings.

As used herein, "conversion" refers to the rate of conversion of a multireactive species having multiple reaction sites with a corresponding reactant. Conversion may be complete, in which all n sites of a multireactive species are reacted with reactant such as a fatty reactant, or only a subset of sites is reacted (n−1, n−2, etc.). For example, amidoamine emulsifiers may be generated from the reaction of a polyamine having multiple amines with a carboxylic acid to form one or multiple amide bonds.

As used herein, "multiamide" refers to a chemical compound having two or more amide bonds generated from a reaction of a multireactive species and one or more reactants, such as a monofunctional reactant. For example, an amidoamine prepared from the reaction of a diamine and a fatty acid may be referred to herein as a multiamide. Multiamides also include the products of a reaction between a multiacid having two or more carboxylic acids (or acid chlorides) and multiple equivalents of an amine such as a fatty amine. Multiamides of the present disclosure are distinct from polyamides created by the polymerization of monomeric diacids and diamines, in that they do not contain a repeating unit structure, as in Nylon 66 for example.

As used herein, "multireactive species" or "multireactive nucleus" refer to molecules having more than one reactive site that may form a covalent bond with a second species. For example, multireactive species include a diamine or polyamine having two or more free primary or secondary amines for reaction with another species. Similarly, a multireactive species may contain one or more electrophilic groups such as carboxylic acids that may react with another species such as an amine.

Reactions involving multireactive species may be used to produce a number of additives useful in the context of wellbore operations, including the production of emulsifiers that stabilize wellbore fluid emulsions and maintain various fluid performance properties. During reaction progress, wellbore fluid additives produced from multireactive species are characterized by a number of possible metrics, including measuring free amine number and carboxylic acid number, depending on the functional groups present on the initial reactants. However, methods to measure these metrics, particularly, on the industrial scale can be costly and time consuming, thus there is pressure to focus on quantification using quick techniques that may not be sensitive enough to important intermediates, which can result in incomplete conversion to the final products and batch-to-batch variations. While these variations may be difficult to detect analytically, but result in substantial changes in performance in the field. Insufficient conversion of reactants to products may result in, for example, poor HPHT filtration with water in filtrate, increased rheology, reaction and dispersion of drill solids such as clays, sensitivity to drill solid concentration, and rheological property changes after extended exposure to elevated temperatures.

Methods in accordance with the present disclosure may be used to track conversion to provide consistent performance for a number of wellbore fluid additives and industrial products. For emulsifiers and other surfactants, variations in the level of conversion may have a direct correlation with performance properties, because unreacted sites present in the constituent multireactive nucleus may be susceptible to ionization states that adversely affect emulsifier performance, in addition to providing sites for unwanted byproduct formation, particularly at elevated temperatures and pressures.

In some embodiments, methods in accordance with the present disclosure may be used to verify reaction progress as measured by other standard commercial methods. For example, it may be desirable to verify a reported amine number provided by a commercial manufacturer where a particular product is known to produce byproducts and/or intermediates that form nonvolatile salts or other species that are often correlated with inconsistent analytical results. Accurate determination of amine number in the context of emulsifiers may aid end users by permitting formulations to be designed with greater degrees of predictability and reproducibility, which then allows for consistent downstream product performance. In addition to free amine determination, methods in accordance with the present disclosure may be used to track amine number, residual fatty acids, and fatty reagents such as maleic and fumaric acid, all of which are part of process control and may be utilized to optimize the composition of the end product.

In one or more embodiments, methods in accordance with the present disclosure may be used to track the rate of conversion in reactions containing multireactive species by silylating leftover reactive sites following an initial amide-forming reaction. Using an amidoamine as an example, the reaction proceeds through an amide-forming reaction between a polyamine and a fatty acid. Amidoamines are one type of emulsifier that may be used to stabilize invert emulsions and other types of oil-based muds (OBM), while also providing fluid stability under downhole conditions. In some embodiments, amidoamines may be prepared from a reaction of diethylenetriamine (DETA) or triethylenetetramine (TETA) with fatty acids and difunctional acids.

A general scheme for the synthesis of an amidoamine emulsifier is shown as Eq. 1, where FA is a fatty acid and MA is maleic anhydride.

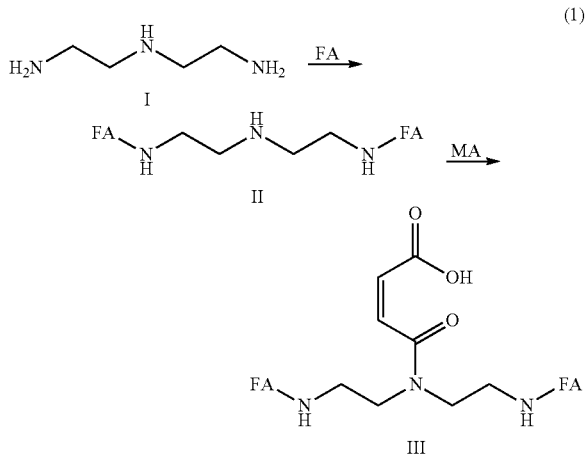

While reaction scheme in Eq. (1) is presented as a series of complete conversions, the final reaction product III may contain substantial concentrations of reactants (residual free amines and fatty acids) and intermediate species. In some embodiments, assays incorporating silyl derivatization may be used as part of a general approach to identify sources of run-by-run inconsistencies in chemical formulations by quantifying incomplete reaction products and calculating mass balance of the transformation. For example, in the amidoamine synthesis presented in Eq. (1), amine values determined by spectroscopic and aqueous titration methods may be verified for accuracy, prior to further reaction to prevent unwanted side reactions and poor performance during scaled-up syntheses. Verifying the amine number also prevents downstream issues when the amidoamine compound is used in more complex formulations in the field.

Methods in accordance with the present disclosure may overcome some of the limitations associated with standard quality control techniques in industrial reagent synthesis. In chemical syntheses involving multireactive species, incomplete reactions may produce completely reacted products, partially reacted multireactive species having one or more free reactive sites, and may also leave substantial quantities of the initial reactants in the product mixture. Given the size limitations of standard gas chromatography (GC) columns, large molecular weight species are difficult to analyze using such techniques.

In one or more embodiments, these limitations may be overcome by quantifying free amine number using GC techniques to analyzing lower molecular weight species such as reactants and degradation products. For example, where the stoichiometric quantity of the multireactive species and added reactants is known, the concentration of the remaining reactant may be used as a proxy for the remaining reactive amine.

However, the presence of the initial reactants in a final product mixture may be difficult to quantify by GC and gas chromatography-mass spectroscopy (GC-MS), because the reactants may include polar acids or non-volatile salts that do not behave predictably in GC columns. For example, as shown in Eq. (2), the reaction in Eq. (1) forms an amidoamine product and, depending on reaction conditions, some quantity of unreacted amidoamine and maleic acid that are stabilized as a salt complex. The salt complex is relatively stable and may not be detectable in appreciable quantities, which can hinder measurement of maleic acid concentration and, in effect, the determination of free amine number.

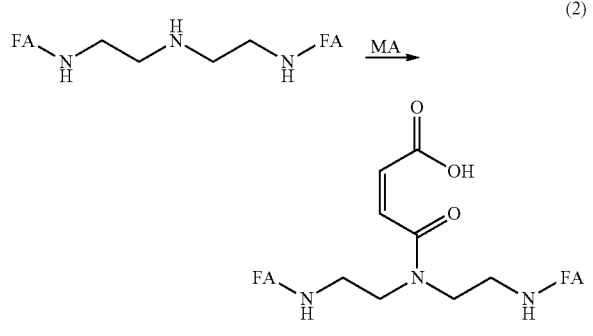

(2)

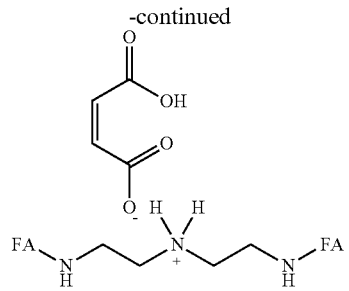

In one or more embodiments, methods of determining the concentration of residual free amines and/or free carboxylic acids in accordance with the present disclosure may include silylation of the species to the respective silylated counterparts. The silylated species are nonionized, more volatile, and easily identifiable by chromatography techniques such as GC, GC-MS, and HPLC.

An embodiment of a silylization method in accordance with the present disclosure is shown in Eq. (3) in which silylating agent N,O-bis(trimethylsilyl)trifluoroacetamide (BSTFA) is reacted with unreacted species, represented as H—Y—R, where Y is a nucleophilic species such as O, S, NH, NR, or COO; and R is alkyl or aryl.

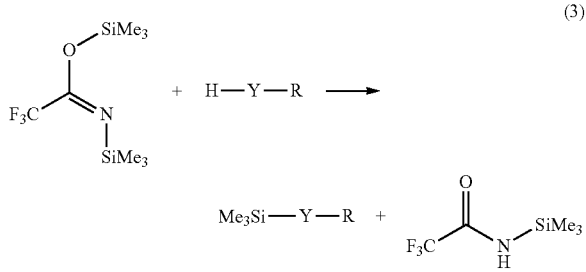

(3)

When analyzed by GC or GC-MS, the silylated species in Eq. (3) may be quantified and used as a proxy for the amount of free amines and/or free carboxylic acids present in the final product of Eq. 1. In some embodiments, the concentration of silylated reagent may also be used to derive an accurate or corrected amine number for the final product by aiding the measurement of remaining reactants and other proxies for reactive amine concentration.

Silylating Agents

Silylating agents in accordance with the present disclosure include silanes and activated silanes capable of reacting with nucleophilic species having one or more active hydrogens, including OH, COOH, NH, $NH_2$, and SH. During silylation, active hydrogens are replaced by an alkylsilyl group, such as trimethylsilane (TMS). Compared to their parent compounds, silyl derivatives are generally are more volatile, less polar, and more thermally stable. The reaction order of silylating agents with nucleophilic groups may generally follow the order of alcohols>phenols>carboxylic acids>1° amines>2° amines>amides.

Silylating agents in accordance with the present disclosure may include N,O-bis(trimethylsilyl)acetamide (BSA), N,O-bis(trimethylsilyl)trifluoroacetamide (BSTFA), N-methyl-N-(tert-butyldimethylsilyl)trifluoroacetamide (MTBSTFA), and pentafluorophenyldimethylsilyl (flophemesyl), N-Methyl-N-trimethylsilylacetamide (MSA), N,O-bis(trimethylsilyl)carbamate (BSC), N,N-bis (trimethylsilyl)formamide, (BSF), N,N'-bis(trimethylsilyl) urea (BSU), N-Methyl-N-trimethylsilylheptafluorobutyramide (MSHFBA), hexamethlydisilazane (HMDS), and the like. In some embodiments, a mixture of silylating agents may be used. For example, trimethylsilylchlorine may be mixed together with a trimethylsilylimdiazole compound and either a silylated trifluoroacetamide or a silylated acetamide.

Nonaqueous Titration

In one or more embodiments, methods of quantifying the rate of conversion of multireactive species in accordance with the present disclosure may include nonaqueous titration to determine the concentration of the residual free amine and/or free carboxylic acid. In some embodiments, nonaqueous titration may be used to determine free amine number, particularly when analyzing complex mixtures of components having varying degrees of solubility in standard solvents used in aqueous titrations.

Generally, nonaqueous titration is the titration of substances dissolved in solvents other than water. Nonaqueous titrations in accordance with the present disclosure may be suitable for the titration of weak acids and weak bases in solvent systems in which organic compounds are most soluble. By titrating product mixtures in accordance with the present disclosure using nonaqueous conditions, materials such as fatty reagents and larger products may be titrated in solvent systems in which the components have optimum or near optimum solubility profiles.

In one or more embodiments, nonaqueous titrations may be measured using a pH electrode with a sensitivity on the scale of millivolts. In other embodiments, nonaqueous titrations may be performed colorimetrically using known pH indicators such as phenolphthalein, neutral red, p-naphtholbenzein, m-cresolsulfonephthalein, and the like.

Nonaqueous titrations may be done in any suitable nonaqueous solvents such as acids including glacial acetic acid, organic solvents such as dioxane, benzene, toluene, chloroform, perchloroethylene, and the like.

In one or more embodiments, nonaqueous titrations may be performed with a titrating agent such as perchloric acid, perchloric dissolved in glacial acetic acid, anhydrous hydrochloric acid in dioxane, sulfuric acid, and the like.

Multireactive Species and Fatty Reagents

In one or more embodiments, methods in accordance with the present disclosure may be used to determine the rate of conversion for complex reactions between a multireactive species and a reactant such as fatty reactants. In a particular example, amidoamine surfactants may be generated from the reaction of a multireactive species and a fatty reagent. Other complex reactions may include reactions of polyacids and other multireactive species with amine-containing fatty reactants. For example, methods in accordance with the present disclosure may be used to quantify the conversion of multireactive species such as quebracho and other polyphenols when reacted with nucleophiles including fatty amines.

Multireactive species in accordance with the present disclosure may include multireactive species such as polyamines. As used herein, "polyamine" refers to a compound having two or more amine functional groups, including primary or secondary amines, available to react with additional compounds. The amine functional groups may be pendant groups off of a carbon backbone in some embodiments, or may be heteroatoms within a carbon chain in other embodiments. In one or more embodiments, polyamines may include diethanolamine, triethanolamine, diethylenetriamine (DETA), triethylenetetramine (TETA), tetraethylenepentamine (TEPA), pentaethylenehexamine (PEHA), and other polyethylene polyamines. Polyamines may include linear or branched organophilic C6-C36 fatty polyamines including polyaliphatic polyamines, heterocyclic polyamines, and alkylalkanol polyamines.

Multireactive species in accordance with the present disclosure may include polyacids in some embodiments. As used herein, "polyacid" refers to a compound having two or more carboxylic acid functional groups available to react with additional compounds. The carboxylic acid functional groups may be pendant groups off of a carbon backbone in some embodiments, or on carbon chains branching off of the carbon backbone in some embodiments.

In one or more embodiments, multireactive species may include linear and branched, saturated and unsaturated C6-C36 fatty polyacids such as oxalic acid, malonic acid, glutaric acid, adipic acid, pimelic acid, suberic acid, azelaic acid, sebacic acid, undecanedioic acid, dodecendioic acid, tridecanedioic acid, tetradecanedioic acid, pentadecanedioic acid, hexadecanedioic acid, citric acid, maleic acid, fumaric acid, and the like.

Fatty reactants in accordance with the present disclosure may include species having the general formula of X—R, where X is a functional group selected from primary and secondary amines, alcohols, thiols, sulfinic acids, sulfonic acids, and carboxylic acids; and R is a saturated and unsaturated, branched and linear, carbon chain having at a carbon number of C6-C30. In some embodiments, the fatty reactant may be one or more fatty acids, including C6-C30 fatty acids such as lauric acid, myristic acid, palmitic acid, stearic acid, oleic acid, or linoleic acid; C6-C30 alkenyl acids, C6-C30 arylalkyl acids, and C6-C30 cycloalkyl acid. In some embodiments, the fatty reactant may include saturated and unsaturated, branched and linear, fatty amines such as a C6-30 alkyl amine, C6-C30 alkenyl amine, C6-C30 arylalkyl amine, and C6-C30 cycloalkyl amine.

In one or more embodiments, multireactive species such as polyamines and polyacids may be reacted with a first reactant that occupies a subset of the total available reactive sites, and then combined with a second reactant that occupies at least a subset of the remaining active sites. Using Eq. (1) as an example, a polyamine (I) may be reacted with a first reactant (a fatty acid in this case), which occupies two reactive amine sites to product multiamide (II). The intermediate (II) may be further reacted with a second reactant (maleic acid) that occupies the remaining secondary amine on the polyamine. Secondary reactants may include any of the fatty reagents discussed above. In addition, secondary reactants may include acids, anhydrides, and esters of C2-C12 acids and polyacids, including maleic acid, fumaric acid, succinic acid, and the like.

Wellbore Fluid Formulations

Wellbore fluids in accordance with the present disclosure include aqueous and oil-based wellbore fluids. In one or more embodiments, wellbore fluids include direct and invert emulsions. In some embodiments, wellbore fluids may include a high internal phase ratio (HIPR) emulsion in which the volume fraction of the internal aqueous phase is a high as 90 to 95 percent. Suitable oil-based or oleaginous fluids may be a natural or synthetic oil and in some embodiments, in some embodiments the oleaginous fluid may be selected from the group including diesel oil; mineral oil; a synthetic oil, such as hydrogenated and unhydrogenated olefins including polyalpha olefins, linear and branch olefins and the like, polydiorganosiloxanes, siloxanes, or organosiloxanes, esters of fatty acids, specifically straight chain, branched and cyclical alkyl ethers of fatty acids, mixtures thereof and similar compounds known to one of skill in the art; and mixtures thereof.

In one or more embodiments, the wellbore fluid may be an invert emulsion having a continuous oleaginous phase and a discontinuous aqueous (or non-oleaginous liquid) phase, among other substances and additives. Non-oleaginous liquids may, in some embodiments, include at least one of fresh water, sea water, brine, mixtures of water and water-soluble organic compounds, and mixtures thereof. In various embodiments, the non-oleaginous fluid may be a brine, which may include seawater, aqueous solutions wherein the salt concentration is less than that of sea water, or aqueous solutions wherein the salt concentration is greater than that of sea water. Salts that may be found in seawater include, but are not limited to, sodium, calcium, aluminum, magnesium, potassium, strontium, and lithium salts of chlorides, bromides, carbonates, iodides, chlorates, bromates, formates, nitrates, oxides, sulfates, silicates, phosphates and fluorides. Salts that may be incorporated in a brine include any one or more of those present in natural seawater or any other organic or inorganic dissolved salts. Additionally, brines that may be used in the drilling fluids disclosed herein may be natural or synthetic, with synthetic brines tending to be much simpler in constitution. In one embodiment, the density of the drilling fluid may be controlled by increasing the salt concentration in the brine (up to saturation). In a particular embodiment, a brine may include halide or carboxylate salts of mono- or divalent cations of metals, such as cesium, potassium, calcium, zinc, and/or sodium.

Wellbore fluids in accordance with the present disclosure may further contain additives. For example, emulsifiers, wetting agents, organophilic clays, viscosifiers, weighting agents, bridging agents, fluid loss control agents, pH buffer, mutual solvents, thinning agents, and corrosion inhibitors may be added to so as to impart additional functional properties.

Applications

Methods in accordance with the present disclosure may be used to quantify the residual free amine and/or free carboxylic acid concentration in a product mixture. In one or more embodiments, methods may be used during formulation or following formulation of a wellbore fluid. For example, a wellbore fluid component prepared from a reaction of a multireactive species and a fatty reactant may be assayed to determine an initial concentration of residual free amine and/or fatty reagent concentration, or to verify a reported concentration. After verification, if the properties of the product are acceptable, the component may be added with the other wellbore fluid components (dispersed in a base fluid, for example) to generate the final wellbore fluid.

In the case of amidoamines and other products prepared from multireactive species, the reported free amine number may be incorrect, depending on the method used. Methods in accordance with the present disclosure may then be used to verify the amine number to determine whether the amount of residual free amine and/or free carboxylic acid is within an acceptable threshold for a given application. As discussed in the following examples, unreacted residual free amine may cause a number of side reactions when added to a wellbore fluid formulation, leading to inconsistent performance between wellbore fluid formulations between batches. Calculation of the actual free amine number for a fluid component may enable operators to save time and funds by mitigating potential issues at the formulation stage and prior to deployment in the field. For example, assaying for amine number using methods in accordance with the present disclosure may allow an operator to select a different product source, modify the reaction conditions, or allow a product to react further achieve the desired amine number (by heating, adding additional reactant, and the like).

Methods in accordance with the present disclosure may be used during the formulation of a wellbore fluid to verify that the concentration for the free amine concentration for a product is within an acceptable threshold for a given application. Acceptable thresholds may be based on industry or proprietary standards for product performance. Turning again to the amidoamine example, amidoamines function as surfactants in some formulations, and incomplete reaction products in the mixture can lead to poorly performing wellbore fluids, unstable emulsions, increased viscosity, and the formation of various byproducts. For example, while unreacted or partially reacted amidoamines and fatty reactants may form complexes that exhibit acceptable emulsification at low temperatures, the complexes dissociate a higher temperatures, leading to unpredictable fluid performance downhole. Thus, accurate determination of the free amine number is desirable to enhance reproducibility and reliability of the wellbore fluid. In one or more embodiments, an acceptable threshold may be a free amine number having a lower limit selected from any of 0, 5, 10, or 15, to an upper limit selected from any of 20, 30, 50, 100, 200, 300, or 400, where any lower limit may be paired with any upper limit. In some embodiments, the acceptable threshold may be a free amine number in the range of 0 to 400, from 0 to 350, or the free amine value may be 0.

In one or more embodiments, methods in accordance with the present disclosure may be used to measure the concentration of free fatty acid in a product mixture, which may be taken in to consideration for the final formulation of a wellbore fluid. Using amidoamine emulsifiers as an example, a polyamine may be reacted with a fatty acid to generate an amidoamine emulsifier and often a mixture of partially reacted components and reactants. Wellbore fluid formulations may use fatty acid components to modify various wetting properties of the final fluid, but can have negative impacts on fluid rheology such as increased sag and decreased viscosity when the concentration becomes excessive. Thus, accurate characterization of the fatty acid content of the respective additives may prevent the addition of too much fatty acid and avoid the associated negative properties.

Methods in accordance with the present disclosure may include the steps of determining free carboxylic acid concentration, and adjusting the concentration of the fatty acid in the wellbore to a concentration within the range of 0 ppb to 1.5 ppb in some embodiments, and from 0.25 ppb to 1.25 ppb in other embodiments.

EXAMPLES

Example 1—Standard Amine Number Calculation

The conversion of a multireactive species in accordance with the present disclosure may be monitored by measuring the concentration of the remaining amines present in the polyamine reactant. Explanation of amine number calculation is given below.

Amine number may be expressed in terms of mg KOH/gram of product, as determined by acid-neutralizing the free amine in the product mixture and back-titrating with KOH. Each amine group reacts in 1:1 molar ratio with acid and it takes 1 mole of KOH to neutralize the salt. In combination with the molar concentration of amine per gram of material, a theoretical amine value may be calculated (expressed as mg KOH/gram) by multiplying the moles of amine by 56 (molecular mass of KOH).

An example of an amine number calculation for the amidoamine reaction in Eq. (1) is shown in Eq. (4). Two cases are given—when 2 moles of oleic acid are mixed with 1 mole of DETA (3 moles of amine) and Eq. (5) provides the theoretical amine number after reaction occurs. Without reaction, amine number of the mix is 251 mg KOH/gram as shown in Eq. (4). If reaction of fatty acid and DETA occurs as planned, then amine value of the product is 88 mg KOH/gram as shown in Eq. (5).

$$\frac{3 \text{ moles amine}}{2*283\frac{g}{mol}(oleic) + 103\frac{g}{mol}(DETA)} * 56\frac{g}{mol}(KOH) = \quad (4)$$

$$251 \text{ mg}\frac{KOH}{gram} \text{ of product}$$

$$\frac{1 \text{ moles amine}}{2*283\frac{g}{mol}(oleic) + 103\frac{g}{mol}(DETA) - 2*18\frac{g}{mol}(water)} * \quad (5)$$

$$56\frac{g}{mol}(KOH) = 88 \text{ mg}\frac{KOH}{gram} \text{ of product}$$

The amidoamine is moved to a second reaction with maleic acid, a "capping" step, after which the amine value should be zero, indicating that all free amines have been reacted as shown in the final product III of Eq. (1). Calculation follows a similar logic described above, however a zero in the numerator for "moles of amine" results in overall zero amine number regardless of molecular weight of the final product. Under ideal conditions, the amine number should be zero at the end of the reaction because an excess of maleic acid to react with all amines in DETA. However, reaction efficiency is rarely complete, and the amine number is non-zero. Based on amine number reported for each product, the rate of conversion for each of the reactions can be evaluated.

Eq. (6) provides an amine number calculation for a reaction step when maleic anhydride is added but reaction did not occur. As shown in the calculation, the amine number decreases to 77 mg KOH/gram because the molecular weight of product increased, despite the moles of amine remaining the same.

$$\frac{1 \text{ moles amine}}{2*283\frac{g}{mol}(oleic) + 103\frac{g}{mol}(DETA) - 2*18\frac{g}{mol}(water) + 98\frac{g}{mol}(MA)} * \quad (6)$$

$$56\frac{g}{mol}(KOH) = 77 \text{ mg}\frac{KOH}{gram}$$

Example 2—Effect of Amine Number on Emulsifier Performance

An example of how incomplete reaction affects emulsifier performance is shown in Table 1. The example uses Product II, amidoamine product prepared from DETA and oleic acid, and Product III, Product II reacted with maleic acid. The results for Product III were compared with an "incomplete" product prepared from a blend of 80% Product III and 20% Product II to simulate what happens if capping step with the di-acid is incomplete.

TABLE 1

Wellbore fluid formulation for Example 2.

| Component | Mass, g |
| --- | --- |
| SYNTHETIC B | 157 |
| VG PLUS | 1.75 |
| lime | 5 |
| Product III OR | 12.5 |
| Blend 80% Product III and 20% Product II | |
| SUREWET | 1 |
| RHEFLAT PLUS | 1 |
| ECOTROL L | 3 |
| 25% CaCl$_2$ Brine | 89 |
| M-I WATE | 284 |
| rheology modifier | 1.25 |
| simulated drilling solids | 35 |

Rheological properties of the wellbore fluids formulated in Table 1 were obtained using a Fann 35 viscometer as shown in Table 2. As the data shows, the incomplete product represented by the mixture of Product II and Product III can exhibit higher rheology, worse HPHT performance, and/or worse electrical stability (ES; an indication of emulsion stability) following the hot roll. In example 2, ES was worse for the mixture of Product II and III (effectively a higher amine number) at HPHT. The mixture also exhibited an accumulation of water in the filtrate, which is undesirable and indicates emulsion instability.

TABLE 2

Rheology of wellbore fluid formulations from Table 1.

| | Product III alone | | | | Product II and III Blend | | | |
| --- | --- | --- | --- | --- | --- | --- | --- | --- |
| | 150° F. before hot roll | 40° F. | 100° F. | 150° F. | 150° F. before hot roll | 40° F. | 100° F. | 150° F. |
| 600 | 68 | 224 | 104 | 75 | 78 | 236 | 112 | 77 |
| 300 | 43 | 128 | 64 | 48 | 51 | 142 | 71 | 49 |
| 200 | 35 | 94 | 48 | 39 | 40 | 117 | 52 | 38 |
| 100 | 26 | 58 | 34 | 30 | 29 | 68 | 39 | 27 |
| 6 | 13 | 17 | 17 | 17 | 13 | 20 | 17 | 12 |
| 3 | 13 | 16 | 17 | 17 | 12 | 18 | 17 | 12 |
| PV | 25 | 96 | 40 | 27 | 27 | 94 | 41 | 28 |
| YP | 18 | 32 | 24 | 21 | 24 | 48 | 30 | 21 |
| 10" Gels | 14 | 17 | 17 | 16 | 12 | 20 | 17 | 12 |

TABLE 2-continued

Rheology of wellbore fluid formulations from Table 1.

| | Product III alone | | | | Product II and III Blend | | | |
|---|---|---|---|---|---|---|---|---|
| | 150° F. before hot roll | 40° F. | 100° F. | 150° F. | 150° F. before hot roll | 40° F. | 100° F. | 150° F. |
| 10' Gels | 21 | 33 | 29 | 24 | 19 | 32 | 26 | 20 |
| ES | 362 | | | 524 | 360 | | | 322 |
| HTHP at 250° F. | | | | 6.8 | | | | 6.8 |
| Water | | | | 0.0 | | | | 0.15 |

Furthermore, not only does incomplete capping reaction affect fluid performance as shown in Table 2, but variations in amine number also impact the ability of the wellbore fluid to inhibit shale dispersion. As shown in Table 3, the amine number for a number of amidoamine emulsifiers shows positive correlation with shale dispersion. Inhibiting shale dispersion is important for fluid performance, and proper quantification of amine number is one element of predicting future performance for wellbore fluids.

TABLE 3

Effect of amine number on shale dispersion for a number of emulsifiers.

| Sample Number | % shale recovery | Amine # mg KOH/gram |
|---|---|---|
| 1 | 116 | 0 |
| 2 | 105 | 9.76 |
| 3 | 101 | 11.5 |
| 4 | 100 | 16.7 |
| 5 | 98 | 7.26 |
| 6 | 96 | 14.3 |
| 7 | 60 | 72.2 |
| 8 | 35 | 28.7 |
| 9 | 31 | 90.5 |
| 10 | 30 | 316 |
| 11 | 30 | 34.3 |
| 12 | 25 | 27.2 |
| 13 | 23.8 | 58.89 |
| 14 | 0 | 306 |

Example 3—Silylation to Quantify Amine Conversion of Amidoamine

In the next example, amine number for a sample amidoamine product is verified by first preparing silyl derivatives of the unreacted amines and carboxylic acid species. Under normal conditions, analysis for excess acids by GC-MS is not straight forward. For one, acids are highly polar species and tend to stick inside the GC column. Second, if amide formation does not occur, acid is still present in the salt form with the ammonium form of the corresponding free amine as shown in Eq. (2), for example. Acids, when in salt form, are not volatile. Furthermore, it is known that maleic acid upon exposure to heat (130° C.) converts to maleic anhydride. This reaction could happen in GC injection inlet (at 250° C.) so it may give false appearance of maleic anhydride in the system. Efficiency of this conversion is not known so quantification of analyte is difficult.

To make acids more volatile and unable to chemically transform during analysis (from maleic acid to maleic anhydride, for example), derivatization using BSTFA is used. With particular respect to Eq. (3), silylating reagents such as BSTFA add a trimethyl silyl group to the carboxylic acid functional group of the acid making it less reactive. It also converts the salt species into a neutral and volatile species.

In this example, sample acids oleic acid and maleic acid concentrations were assayed using silyl derivitization. Derivitization was performed by mixing the analyte with BSTFA (50 mg analyte+1 g BSTFA) and heating to 160° F. for 1 hour. The sample was then diluted in an organic solvent methylene chloride.

Improvements in analysis using the silylization method are seen in Table 4. With the BSTFA derivative, signal from 1 mg/ml of oleic acid is ~40 times stronger signifying better detection of analyte, while maleic acid did not produce any signal prior to derivitization.

TABLE 4

GC-MS response for acids and for BSTFA derivatives. GC-MS signal strength is normalized per 1 mg/mL analyte.

| Product | Signal strength (normalized for concentration) |
|---|---|
| Oleic acid | 1.22 |
| Maleic acid | n/a (did not dissolve) |
| Oleic acid BSTFA | 44 |
| Maleic acid BSTFA | 30 |

Maleic anhydride does not react with BSTFA, therefore post-derivatization the concentration of maleic anhydride, maleic acid, and oleic acid can each be independently accounted for.

Figure 2:
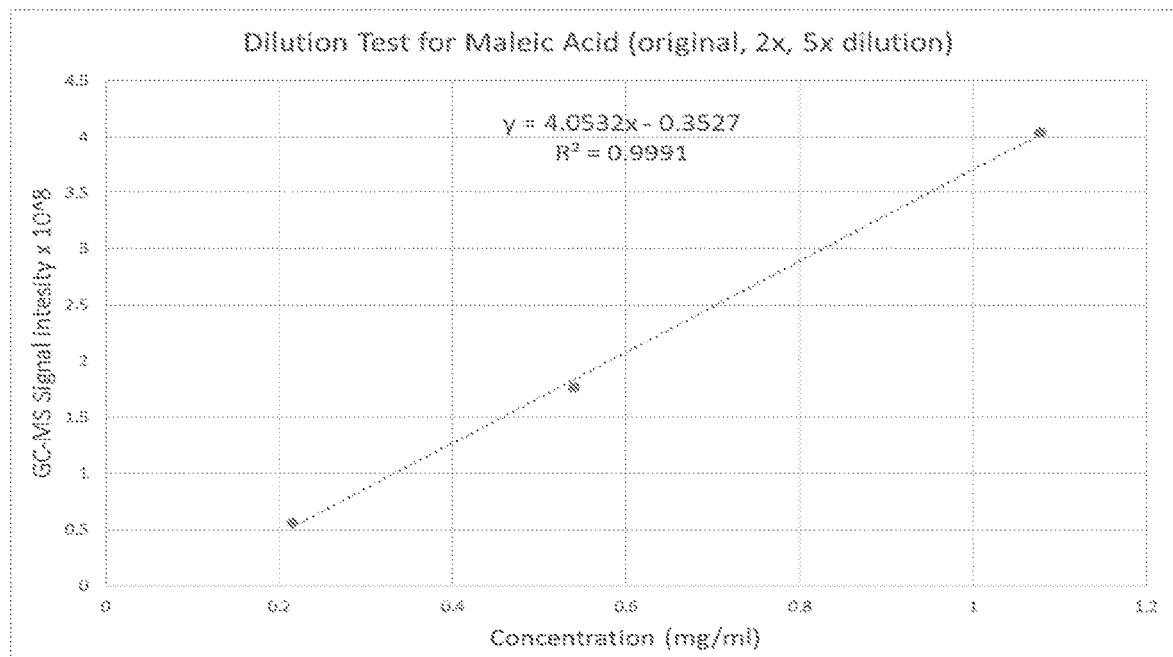

As proof of concept, FIG. 1 shows a calibration curve of BSTFA derivative of oleic acid shown with a linear response when diluted 2× and 5× from an initial starting concentration. With particular respect to FIG. 2, a calibration curve of BSTFA derivative of maleic acid is shown with a strong linear correlation when diluted 2× and 5× from an initial starting concentration.

Example 4—Nonaqueous Titration

As discussed above, amine values are relevant to the determination of overall reaction progress, in addition to being an indicator of later performance for certain wellbore chemicals such as emulsifiers. However, standard aqueous titration techniques have provided inconsistent measurements in laboratory testing.

In the next example, nonaqueous titration is used to assay a number of samples, which has demonstrated greater accuracy and increased reproducibility. During nonaqueous titration experiments, an amidoamine sample is dissolved in glacial acetic acid. ~500 mg/50 ml. Solution is titrated with 0.1N $HClO_4$ in glacial acetic acid. Titration progress is tracked with pH electrode set to millivolt measurement scale. As titration reached an equivalence point, there was a large change is electrode reading. A derivative for the volume of titrant added vs millivolt reading was calculated to facilitate the end point identification.

Figure 3:
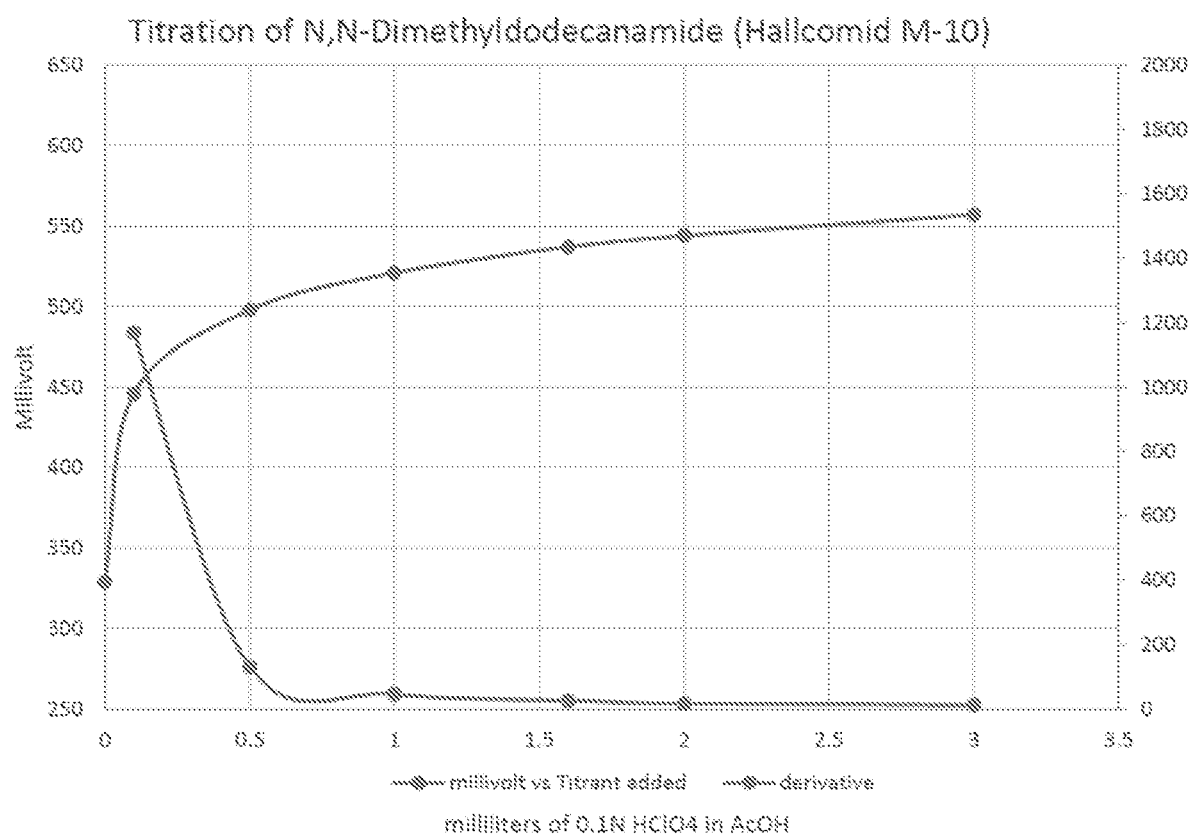
FIGS. 3 and 4 are graphical representations showing the change in response of a pH electrode in millivolts as a function of titrant added during a nonaqueous titration in accordance with embodiments of the present disclosure.

With particular respect to FIG. 3, an example graph of non-aqueous titration of an amidoamine surfactant SUREMUL™ from Schlumberger is shown. The left axis shows the value in millivolts, the right axis shows the derivative value, while the x-axis shows the volume of 0.1 N $HClO_4$ added. The highest derivative reading is at the inflection point and was taken as titration equivalence point. From known amount of amidoamine added and the amount of perchloric acid consumed, an amine number was calculated. As an assurance that this method is accurate, titrations were repeated for products with known amine values and in all cases obtained results that matched reported values. Examples of chemicals tested—diethanolamine, triethanolamine, DETA, and TETA.

Figure 4:
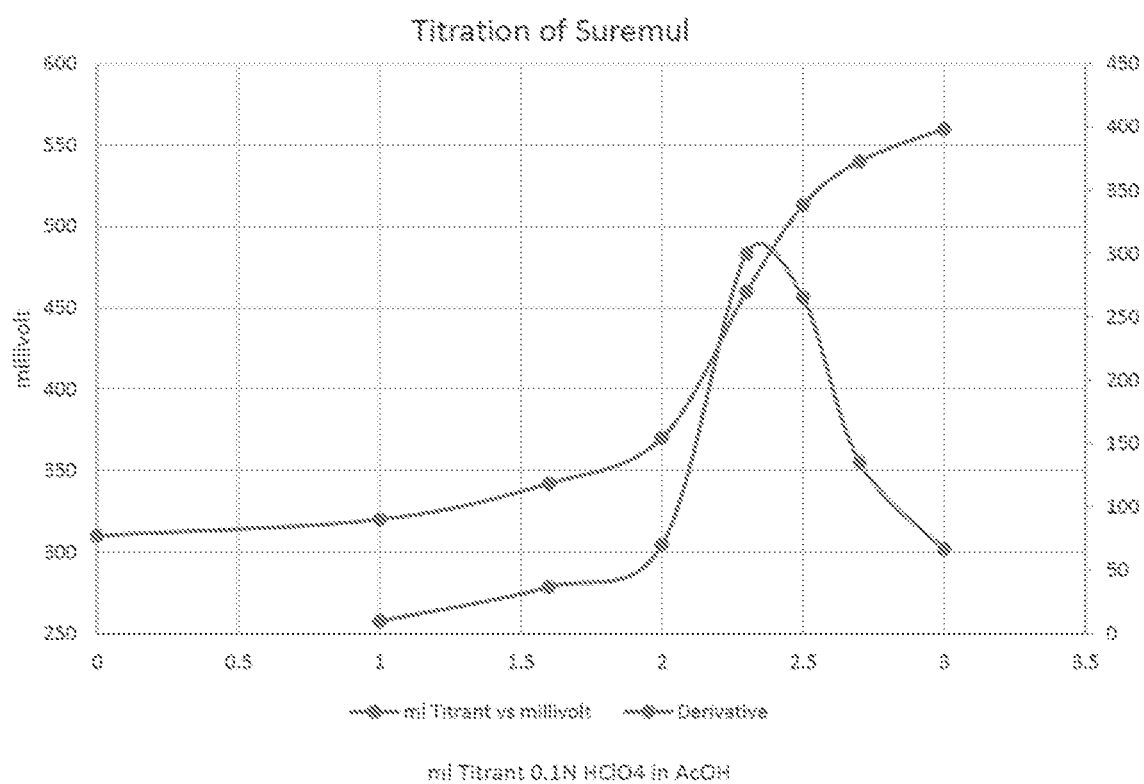

To provide assurance that this method is not subjected to interferences from common additives, test compounds were assayed such as non-ionic surfactant Triton HW-1000 from Dow Chemical, amide Hallcomid M-10 from Stepan Company, and pure solvent. With particular respect to FIG. 4, no interference was observed for Hallcomid M-10, which contained no free amines. Without an analyte with measurable amine value, the mV reading maxes out nearly instantly even when high loading of compound is tested (1 gram of analyte in 50 ml AcOH vs 0.2-0.5 g typical for compound with amine value).

In example shown in FIG. 3, the amine value for SUREMUL™ was calculated 44 mgKOH/gram (100% active basis), while the batch was reported to contain an amine value of 24 mgKOH/gram (100% active basis) using a different titration method. The discrepancy in amine value measurement by two different methods may be related to incomplete maleic anhydride reaction, which leads to the formation of the shown in Eq. (2) that hinder accurate free amine measurement. Amines are weak acids and mixed with weak bases, a buffer system is formed. Buffers, by the definition, is a system that resists change in pH. Because conventional titration tracks pH, it cannot accurately titrate amines in a buffer system.

Partial confirmation of this issue is seen in Table 5. Polyamine A and Product II from Eq. (1) do not have maleic acid added and conventional titration matches non-aqueous titration values. However, Emulsifier A and SUREMUL™ contain residual maleic acid and the result clearly shows a deviation in the free amine value. This suggests that presence of unreacted maleic may give a false positive that the reaction is complete, while remaining incomplete by some degree.

TABLE 8

Amine value comparison for a number of samples.

| Product | Amine Value Reported | Non-Aqueous Titration | Amine Value at 100% Conversion (theory) |
|---|---|---|---|
| Polyamine A | 306 | 304 | 302 |
| Product II from Eq. (1) | 90 | 87 | 88 |
| Emulsifier A | 0 | 40 | 0 |
| SUREMUL ™ (100% solids) | 30 | 44 | 0 |

The importance of amine number analysis shows not only a two-fold discrepancy in the measurement but the implication of this high amine number. Amine number in the range of 40 mgKOH/gram (100% basis) means the intended SUREMUL™ reaction is only 50% complete.

Example 5—Improving Conversion of Amidoamine to a Desired Product

In the next example, methods of quantifying free amines and/or free carboxylic acids in accordance with the present disclosure are used to analyze the progress of a reaction between a multireactive species and a fatty reactant, further techniques are discussed to improve conversion of reactants to products. With particular respect to Eq. (1), the second step of the synthesis is often a bottleneck in the full conversion of reactants to products for a number of reasons including: 1) formation of amine salt between (III) and (II), which slows the reaction at 50% completion; 2) inefficient removal of water generated from the condensation of the polyamine and fatty acid, which slows further amide conversion; and 3) hydrolysis of reactive anhydride anhydride species by excess water.

In one or more embodiments, amidoamine synthesis may be improved by reacting the polyamine and fatty acid at higher temperatures. The reaction to product final product (III) in Eq. (1) will work at temperatures as low as ambient, but reaction progress stops at about 50% conversion. Increasing the temperature to 350° F. can be used to speed up the reaction. Higher temperatures may be possible but at some point ENE reaction between maleic and unsaturated TOFA will occur or maleic polymerization, or other undesirable reactions can occur if temperature is too high. Furthermore, it may be advantageous to gradually increase the temperature during the reaction maleic step because if temperature is raised too high before maleic anhydride is added to produce product (III), because intermediate (II) may cyclize to imidazoline which is undesirable.

In Eq. (1), temperature for the second reaction to produce product (III) may be the same as the first step (in the range of about 300 to 325° F.), where the temperature is selected to achieve fast conversion of the polyamine and the fatty acid, while minimizing byproduct formation. In some embodiments, the temperature may be lower before maleic anhydride addition to decrease maleic sublimation or decomposition. In some embodiments, maleic may be added all at once or in portions.

In some embodiments, the concentration of the fatty acid reactant may be monitored using nonaqueous titration or silylation/GC-MS to ensure reaction progression. Controlling maleic concentration is important and silylation/GC-MS may be used to monitor maleic acid concentration monitor reaction progression. Maleic quantity may be important because product is (III) in Eq. (1) has acid functionality and if not enough maleic is present, it can react with intermediate (II) and form a polyamide which is not a good emulsifier. Thus, tracking maleic content and adjusting it may improve the of product (III).

In some embodiments, reaction time may be increased to increase conversion to products. Another method to improve yield of product (III) in Eq. 1 is longer reaction time. Longer reaction time will allow reaction to proceed to completion also it will allow for water that was generated in the condensation reaction that generates product (II) in Eq. 1 to leave the reactor.

Other techniques may also be employed such as the removal of water generated from the condensation reaction. Removal of excess water generated by condensation reactions may improve reaction efficiency by minimizing the stabilizing interactions and shielding effects produced by interaction of the reactants and intermediates with water. However, in the context of the amidoamine reaction of Eq. (1), removal of water from the reaction to generate product (II) or (III) may be difficult because of affinity of water to the polar product and intermediates, the high viscosity of the product, and the large scales of typical batch production. The small surface area to volume ratio means water is difficult to remove even at reaction temperatures of 300-350° F. which is far above boiling point of water. In some embodiments, reagents used to sequester and remove water may include desiccating additives such as magnesium sulfate, calcium sulfate, anhydrous sodium sulfate, or zeolitic reagents and other molecular sieves (having 3-4 angstrom pore size, for example).

In one or more embodiments, physical techniques to remove water may include reacting components under vacuum or bubbling nitrogen through the bottom of the reaction vessel. However, the level of vacuum and/or nitrogen injection should be selected to ensure minimal loss of unreacted species having low boiling points. In some embodiments, water concentration in the reaction mixture may be minimized by converting fatty acid reactants to esters prior to reaction with the polyamine. Dehydration reactions generate water, and water may be removed as the reaction progresses or fatty reactants may include esters prepared by reacting a fatty acid with a small chain alcohols. For example, the reaction of a polyamine with a fatty acid methyl ester (FAME) may be used to generate a multiamide, but will produce volatile methanol as opposed to water and may minimize byproduct formation.

In some embodiments, maleic anhydride or maleic acid may be substituted with dimethyl maleate. Dimethylmaleate is easier to handle than maleic anhydride, it is liquid and thus can be pumped into the reactor. The boiling point of dimethyl malate is much higher than maleic anhydride so it won't evaporate from reactor even if bubbling nitrogen through the bottom of the reactor or vacuum is used. On the other hand, when dimethylmaleate reacts with intermediate (II) in Eq. (1), methanol is formed which is more volatile than water. Using dimethylmaleate will produce an ester as final product, which may have lower corrosion properties as compared to acidic product (III). In use, especially high temperature, the ester form of product (III) may convert to acid which is the most desirable active species. In some embodiments, fumaric acid and fumarate esters may also be used in place of maleic acid derivatives, because it has been noted that a portion of maleic acid and products containing maleic acid functional groups isomerizes to fumaric acids at high temperature.

In the next example, the analysis of silylated fatty acid reactants using GC-MS is used to quantify the residual fatty acid reactants (that are otherwise undetectable by GC techniques) in a reaction to produce an amidoamine. Wellbore fluids were formulated using a DETA-based amidoamine obtained from various suppliers as shown in Table 9. A series of samples were prepared using different batches of the DETA-based amidoamine emulsifier obtained from a supplier, and rheology was measured for each of the samples at various temperatures, before and after dynamic heat aging by hot roll.

TABLE 9

15 ppg 80-20 Test Formulation Used for Evaluation of a DETA-based amidoamine emulsifier.

| | |
|---|---|
| SYNTHETIC B, g | 152 |
| VG HT, g | 3 |
| Lime, g | 5 |
| DUROGEL, g | 15 |
| DETA-based amidoamine emulsifier | 12 |
| SUREWET | 1 |
| ECOTROL HT, g | 3 |
| 25% CaCl2 Brine, g | 65 |
| M-I WATE, g | 410 |
| rheology modifier, g | 1.25 |

TABLE 10

Rheology of fluids containing DETA-based amidoamine emulsifier

| | Batch #1 | | | Batch #2 | | | Batch #3 | | |
|---|---|---|---|---|---|---|---|---|---|
| | 150 F. | 100 F. | 150 F. | 150 F. | 100 F. | 150 F. | 150 F. | 100 F. | 150 F. |
| 600 | 85 | 127 | 96 | 156 | 165 | 122 | 196 | 181 | 137 |
| 300 | 46 | 74 | 59 | 104 | 113 | 82 | 135 | 111 | 93 |
| 200 | 31 | 55 | 44 | 81 | 81 | 68 | 109 | 87 | 77 |
| 100 | 17 | 35 | 31 | 51 | 55 | 52 | 79 | 59 | 61 |
| 6 | 3 | 12 | 15 | 8 | 31 | 40 | 31 | 32 | 52 |
| 3 | 2 | 12 | 14 | 6 | 31 | 40 | 27 | 31 | 42 |
| PV | 39 | 53 | 37 | 52 | 52 | 40 | 61 | 70 | 44 |
| YP | 7 | 21 | 22 | 52 | 61 | 42 | 74 | 41 | 49 |
| 10" Gels | 3 | 17 | 17 | 9 | 39 | 39 | 28 | 40 | 41 |
| 10' Gels | 5 | 26 | 22 | 43 | 38 | 35 | 62 | 53 | 48 |
| ES | 414 | — | 1140 | 253 | — | 536 | 485 | — | 989 |
| HTHP at 350 F. | — | — | 12 | — | — | 24 | — | — | 21 |
| Water | — | — | 0.2 | — | — | 2 | — | — | 1.4 |

Figure 5:
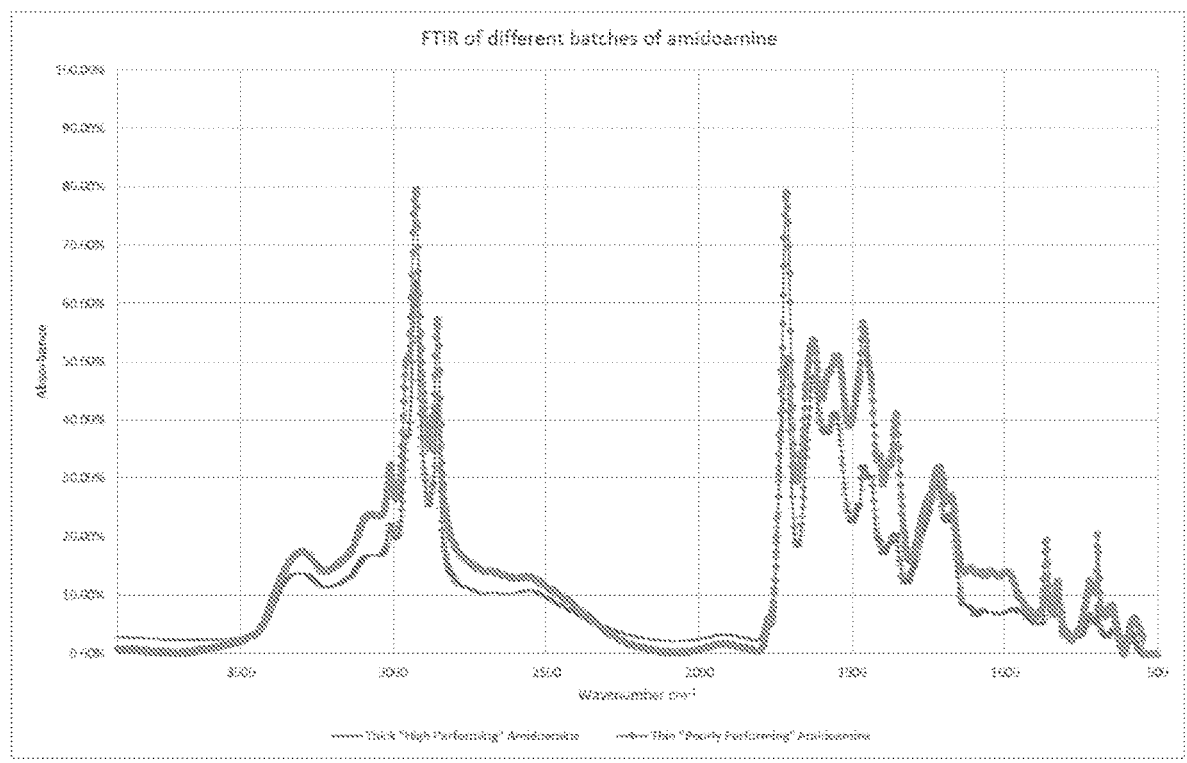
FIG. 5 is a Fourier transform infrared (FTIR) spectrogram of compounds in accordance with embodiments of the present disclosure.

Samples of DETA-based amidoamine emulsifiers characterized as "high performing" or "low performing" based on their performance properties in rheological testing were analyzed using FTIR. A sample spectrum obtained is reproduced as FIG. 5, where comparison of high performing (dashes) and low performing (circles) batches of DETA-based amidoamine emulsifiers show little difference, highlighting the fact that FTIR tracking for these products and amidoamines in general are susceptible to error in the calculation of free amine.

Figure 6:
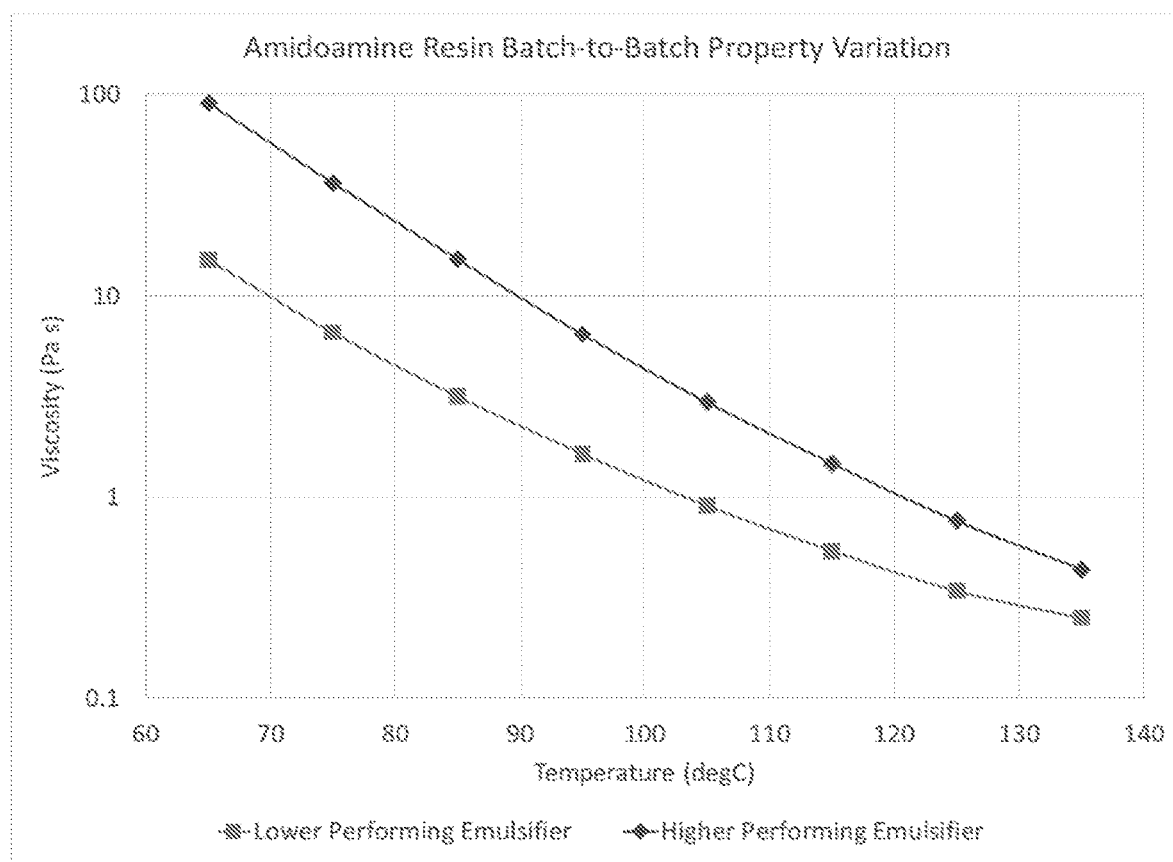
FIG. 6 is a graphical representation of viscosity as a function of temperature for a number of samples in accordance with embodiments of the present disclosure.

In the next example, viscosity is used as an indicator to track conversion of intermediates to products. With particular respect to FIG. 6, viscosity discrepancies between batches "higher performing" emulsifier (diamonds) and "lower performing" emulsifier (circles) may indicate that the synthesis reaction to produce the "lower performing" emulsifier is not complete. In some embodiments, viscosity may be used as a secondary method of tracking product quality after conversion, but may be paired with another method of analysis such as non-aqueous titration, because viscosity greatly depends on accurate solids content. It is also noted that viscosity does not follow a linear profile during course of reaction. Initially, viscosity is high due to amine-acid salt formation, but may drop as the condensation reaction proceeds. Finally, viscosity may begin to increase as the reaction proceeds to complete conversion of the reactants, due at least in part to build-up of higher molecular weight species.

Figure 7:
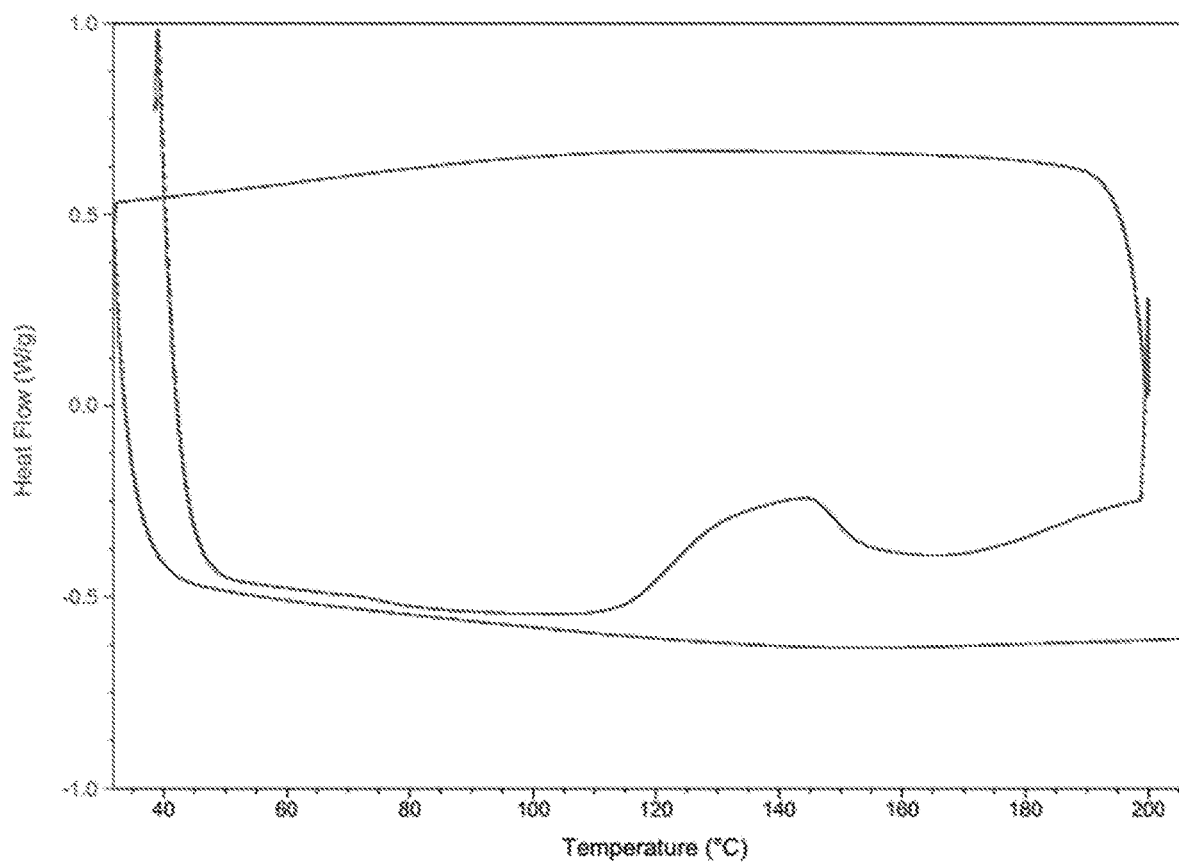
FIG. 7 is a graphical representation of heat flow as a function of temperature for a sample in accordance with embodiments of the present disclosure.

In the next example, differential scanning calorimetry (DSC) was also used to analyze products prepared from amidoamine reactions and other reactions involving multi-reactive species. With particular respect to FIG. 7, a sample of DETA-based amidoamine emulsifier undergoes an exothermic reaction, starting at about 110° C. to about 160° C. This suggests that synthesis reaction of DETA-based amidoamine emulsifier was not completed even though previously reported amine value is zero. At zero amine value no additional reaction is possible so this is another example where commonly used methods such as aqueous titration and FTIR to track conversion of reactants to product is not reliable.

Figure 8:
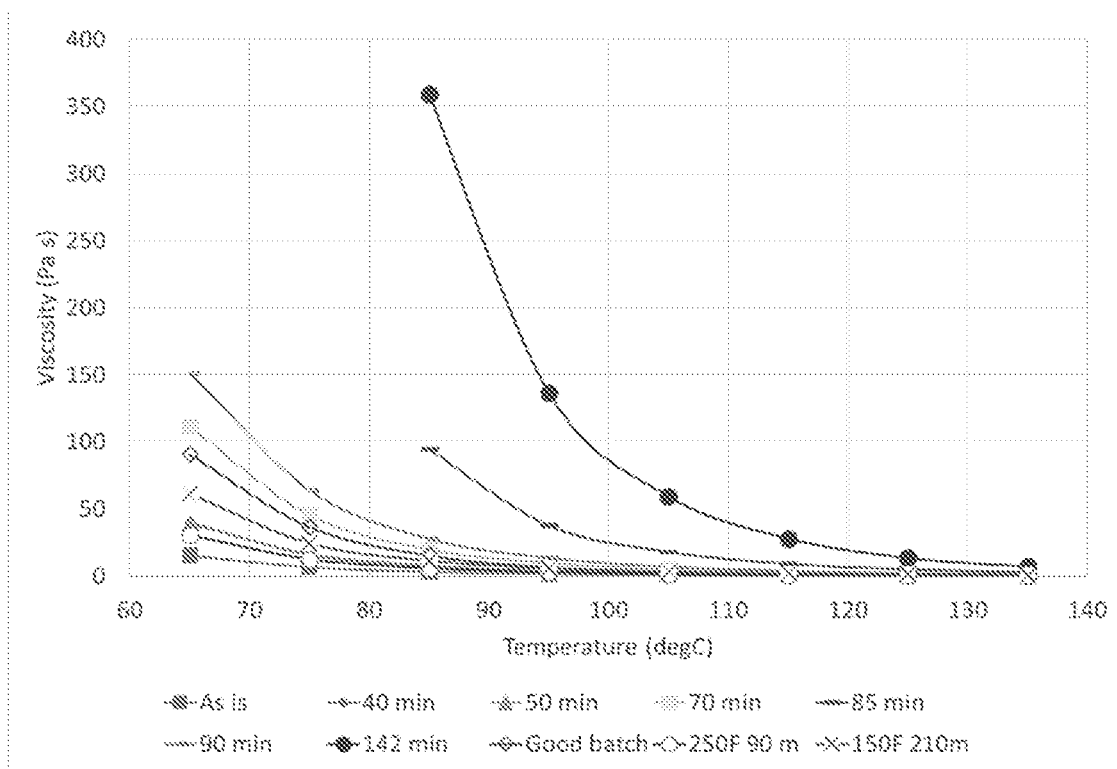
FIG. 8 is a graphical representation of viscosity as a function of temperature for a number of samples in accordance with embodiments of the present disclosure.

In the next example, samples of poorly performing DETA-based amidoamine emulsifier (identified as a mixture of reacted and unreacted materials) were heated in an oven to complete the conversion to the final target product. With particular respect to FIG. 8, the viscosity for various wellbore fluid formulations containing an DETA-based amidoamine emulsifier that was heated for various periods of time and at various temperatures. This observation was counterintuitive since supplier-reported amine value was close to zero suggesting that no further reaction was possible by heating the DETA-based amidoamine emulsifier. In addition, non-aqueous titration was used to confirm that the original amine number for the DETA-based amidoamine emulsifier prior to heating was ~40, indicating substantially incomplete reaction.

These results suggest that consistency of the DETA-based amidoamine emulsifier=has considerable variability, which is likely due to the conventional methods used to tract reaction progress during synthesis of the amidoamine. These findings further highlight importance of appropriate analytical measurements to track performance of emulsifier and develop a product that can be successfully produced in commercial quantities.

In the next example, poorly performing DETA-based amidoamine emulsifier was heated in an oven for various time periods and the rheology was measured using a FANN 35 viscometer to generate the values shown in Table 11.

TABLE 11

Rheology for wellbore fluids containing samples of DETA-based amidoamine emulsifier, before and after heat treatment.

| | poor performing emulsifier | | | 40 min heating | | | 90 min heating | | | 150 min heating | | |
|---|---|---|---|---|---|---|---|---|---|---|---|---|
| | 150 F. | 40 F. | 100 F. | 150 F. | 40 F. | 100 F. | 150 F. | 40 F. | 100 F. | 150 F. | 40 F. | 100 F. | 150 F. |
| 600 | 127 | >300 | 211 | 195 | >300 | 160 | 127 | 268 | 122 | 98 | 278 | 130 | 100 |
| 300 | 72 | 222 | 137 | 138 | 171 | 96 | 86 | 145 | 73 | 62 | 149 | 75 | 62 |
| 200 | 51 | 162 | 110 | 118 | 123 | 74 | 72 | 100 | 55 | 49 | 104 | 55 | 49 |
| 100 | 30 | 102 | 80 | 96 | 71 | 51 | 55 | 54 | 34 | 35 | 56 | 35 | 35 |
| 6 | 4 | 33 | 54 | 81 | 18 | 28 | 42 | 9 | 15 | 22 | 8 | 14 | 21 |
| 3 | 3 | 32 | 52 | 76 | 16 | 28 | 43 | 8 | 14 | 22 | 7 | 13 | 20 |
| PV | 55 | — | 74 | 57 | — | 64 | 41 | 123 | 49 | 36 | 129 | 55 | 38 |
| YP | 17 | — | 63 | 81 | — | 32 | 45 | 22 | 24 | 26 | 20 | 20 | 24 |
| 10" Gels | 5 | 5 | 64 | 67 | 25 | 42 | 43 | 13 | 28 | 27 | 12 | 26 | 27 |
| 10' Gels | 19 | 19 | 76 | 68 | 78 | 61 | 44 | 46 | 37 | 27 | 48 | 37 | 23 |
| ES | 585 | 585 | — | 983 | — | — | 804 | — | — | 953 | — | — | 812 |
| HTHP at 350 F. | — | — | — | 22 | — | — | 15.2 | — | — | 10.6 | — | — | 12 |
| Water | — | — | — | 2 | — | — | 0.6 | — | — | 0.1 | — | — | 0.4 |

The data show that rheology decreased and HPHT improved. Heating time and temperature can be selected from a broad range, generally selected for fastest reaction to occur without causing side reactions, i.e., 120-170° C. This effect is also observed in the DSC data in FIG. 7, where reaction rate is appreciably high at the scanning temperature of 120° C.

Embodiments of the present disclosure may provide at least one of the following advantages. Methods of quantifying residual reactants in accordance with the present disclosure may be useful for tracking additive performance and quality control and conversion monitoring in commercial reagent production. In addition, analytical methods in accordance with the present disclosure may be verifying the results of other testing methods such as FTIR and standard GC-MS without silylation.

Although the preceding description references particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method of formulating a wellbore fluid, the method comprising:
   quantifying the concentration of residual free amine and/or free carboxylic acid in a product mixture prepared from a reaction of a multireactive species and a fatty reactant, wherein the reaction of a multireactive species and a fatty reactant comprises an amide- or imine-forming reaction;
   verifying that the concentration for the free amine and/or free acid in the product mixture is within an acceptable threshold; and
   combining the product mixture with one or more wellbore fluid components to generate the wellbore fluid;
   wherein quantifying the concentration of the residual free amine and/or free carboxylic acid comprises nonaqueous titration.

2. The method of claim 1, wherein quantifying the concentration of the residual free amine and/or free carboxylic acid comprises:
   reacting the product mixture with a silylating agent to convert the residual free amine and/or free carboxylic acid to a respective silylated amine and/or silylated carboxylic acid;
   quantifying the concentration of the silylated amine and/or silylated carboxylic acid; and
   converting the concentration of the silylated amine and/or silylated carboxylic acid to the concentration of residual free amine and/or free carboxylic acid.

3. The method of claim 2, wherein quantifying the concentration the silylated amine and/or silylated carboxylic acid comprises measuring the concentration by gas chromatography (GC).

4. The method of claim 2, wherein quantifying the concentration the silylated amine and/or silylated carboxylic acid comprises measuring the concentration by gas chromatography/mass spectroscopy (GC-MS).

5. The method of claim 2, wherein the silylating agent is one or more selected from a group consisting of N,O-bis(trimethylsilyl)acetamide (BSA), N,O-bis(trimethylsilyl)trifluoroacetamide (BSTFA), N-methyl-N-(tert-butyldimethylsilyl)trifluoroacetamide (MTBSTFA), and pentafluorophenyldimethylsilyl (flophemesyl), N-Methyl-N-trimethylsilylacetamide (MSA), N,O-bis(trimethylsilyl) carbamate (BSC), N,N-bis(trimethylsilyl)formamide, (BSF), N,N'-bis(trimethylsilyl)urea (BSU), N-Methyl-N-trimethylsilylheptafluorobutyramide (MSHFBA), and hexamethlydisilazane (HMDS).

6. The method of claim 1, further comprising adjusting the concentration of the free carboxylic acid in the wellbore to a concentration within the range of 0 ppb to 10 ppb (pounds per barrel).

7. The method of claim 1, wherein the product mixture is further reacted with a second reactant prior to combining the product mixture with one or more wellbore fluid components to generate the wellbore fluid.

8. The method of claim 1, wherein the nonaqueous titration is performed by mixing a portion of the product mixture with glacial acetic acid and titrating with perchloric acid to determine the concentration of the residual free amine.

9. The method of claim 1, the product mixture comprises an emulsifier and wherein quantifying the concentration of residual free amine and/or free carboxylic acid comprises:
   measuring a first viscosity of a fluid composition containing the emulsifier;
   heat aging the fluid; and
   measuring a second viscosity of the fluid composition, wherein a difference between the first viscosity and the second viscosity is indicative of the presence of free amines.

10. A method of formulating a wellbore fluid, the method comprising:
    quantifying, by nonaqueous titration, the concentration of residual free amine in a product mixture prepared from a reaction of a multireactive species and a fatty reactant, wherein the reaction of a multireactive species and a fatty reactant comprises an amide- or imine-forming reaction;
    verifying that the concentration for the residual free amine in the product mixture is within an acceptable threshold; and
    combining the product mixture with one or more wellbore fluid components to generate the wellbore fluid;
    further comprising determining the concentration of free carboxylic acid in the product mixture, and adjusting the concentration of the free carboxylic acid in the wellbore to a concentration within the range of 0 ppb to 10 ppb.

11. The method of claim 10, wherein the nonaqueous titration is performed by mixing a portion of the product mixture with glacial acetic acid and titrating with perchloric acid to determine the concentration of the residual free amine.

12. The method of claim 10, wherein the acceptable threshold of residual free amine is an amine number of 0.

13. The method of claim 10, wherein the acceptable threshold of residual free amine is an amine number in the range of 0 to 30.

14. The method of claim 10, further comprising reacting the product mixture with a second reactant prior to combining the product mixture with one or more wellbore fluid components to generate the wellbore fluid.

15. The method of claim 10, wherein if a product mixture is determined to contain a concentration of residual free amine outside of an acceptable threshold, the method further comprises heating the mixture to further react the product mixture.

16. The method of claim 10, wherein the wellbore fluid is a water-in-oil emulsion.

17. The method of claim 10, wherein the nonaqueous titration comprises measuring the product mixture using a pH electrode.

18. The method of claim 10, wherein the product mixture comprises an amidoamine.

19. A method of monitoring the conversion of a multireactive species, the method comprising:
    reacting the multireactive species and a fatty reactant to generate a product mixture, wherein reacting the multireactive species and a fatty reactant comprises an amide- or imine-forming reaction;
    quantifying the concentration of residual free amine and/or free carboxylic acid in the product mixture;

verifying that the concentration for the free amine and/or free acid in the product mixture is within an acceptable threshold; and collecting the product mixture.

20. The method of claim 19, wherein quantifying the concentration of the residual free amine and/or free carboxylic acid comprises:

reacting the product mixture with a silylating agent to convert the residual free amine and/or free carboxylic acid to a respective silylated amine and/or silylated carboxylic acid;

quantifying the concentration of the silylated amine and/or silylated carboxylic acid; and converting the concentration of the silylated amine and/or silylated carboxylic acid to the concentration of residual free amine and/or free carboxylic acid.

21. The method of claim 20, wherein quantifying the concentration the silylated amine and/or silylated carboxylic acid comprises measuring the concentration by gas chromatography (GC).

22. The method of claim 20, wherein quantifying the concentration the silylated amine and/or silylated carboxylic acid comprises measuring the concentration by gas chromatography/mass spectroscopy (GC-MS).

23. The method of claim 20, wherein the silylating agent is one or more selected from a group consisting of N,O-bis(trimethylsilyl)acetamide (BSA), N,O-bis(trimethylsilyl)trifluoroacetamide (BSTFA), N-methyl-N-(tert-butyldimethylsilyl)trifluoroacetamide (MTBSTFA), and pentafluorophenyldimethylsilyl (flophemesyl), N-Methyl-N-trimethylsilylacetamide (MSA), N,O-bis(trimethylsilyl) carbamate (BSC), N,N-bis(trimethylsilyl)formamide, (BSF), N,N'-bis(trimethylsilyl)urea (BSU), N-Methyl-N-trimethylsilylheptafluorobutyramide (MSHFBA), and hexamethlydisilazane (HMDS).

24. The method of claim 19, further comprising adjusting the concentration of the free carboxylic acid in the wellbore to a concentration within the range of 0 ppb to 10 ppb.

25. The method of claim 19, wherein the product mixture is further reacted with a second reactant prior to combining the product mixture with one or more wellbore fluid components to generate the wellbore fluid.

26. The method of claim 19, wherein quantifying the concentration of the residual free amine and/or free carboxylic acid comprises nonaqueous titration.

27. The method of claim 26, wherein the nonaqueous titration is performed by mixing a portion of the product mixture with glacial acetic acid and titrating with perchloric acid to determine the concentration of the residual free amine.

28. The method of claim 19, the product mixture comprises an emulsifier and wherein quantifying the concentration of residual free amine and/or free carboxylic acid comprises:

measuring a first viscosity of a fluid composition containing the emulsifier;

heat aging the fluid; and measuring a second viscosity of the fluid composition, wherein a difference between the first viscosity and the second viscosity is indicative of the presence of free amines.

* * * * *